US009155852B2

United States Patent
Soliman et al.

(10) Patent No.: US 9,155,852 B2
(45) Date of Patent: Oct. 13, 2015

(54) SYSTEM AND METHOD FOR ADAPTIVE HIGH FREQUENCY FLOW INTERRUPTER CONTROL IN A PATIENT RESPIRATORY VENTILATOR

(71) Applicant: CareFusion 207, Inc., San Diego, CA (US)

(72) Inventors: Ihab S. Soliman, Laguna Niguel, CA (US); Steven Duquette, Laguna Niguel, CA (US)

(73) Assignee: CareFusion 207, Inc., San Diego, CA (US)

( * ) Notice: Subject to any disclaimer, the term of this patent is extended or adjusted under 35 U.S.C. 154(b) by 351 days.

(21) Appl. No.: 13/869,838

(22) Filed: Apr. 24, 2013

(65) Prior Publication Data

US 2013/0319414 A1 Dec. 5, 2013

Related U.S. Application Data

(62) Division of application No. 11/794,675, filed as application No. PCT/US2006/022205 on Jun. 7, 2006, now Pat. No. 8,443,801.

(51) Int. Cl.
*A61M 16/00* (2006.01)
*A61M 16/10* (2006.01)

(52) U.S. Cl.
CPC .......... *A61M 16/00* (2013.01); *A61M 16/0096* (2013.01); *A61M 16/10* (2013.01); *A61M 2016/003* (2013.01); *A61M 2016/0027* (2013.01); *A61M 2205/3334* (2013.01)

(58) Field of Classification Search
CPC ............ A61M 16/10; A61M 16/1005; A61M 2016/0027; A61M 2016/003; A61M 2016/0033; A61M 2016/0036; A61M 2016/0039; A61M 2016/0042; A61M 2016/102; A61M 2016/1025; A61M 2016/103; A61M 2205/33; A61M 2205/3331; A61M 2205/3334
USPC ............ 128/204.21, 204.22, 204.23, 204.29, 128/205.11
See application file for complete search history.

(56) References Cited

U.S. PATENT DOCUMENTS

| | | | |
|---|---|---|---|
| 5,850,835 A | 12/1998 | Takaki et al. | |
| 6,260,550 B1 | 7/2001 | Weismann et al. | |
| 6,422,237 B1 | 7/2002 | Engel et al. | |
| 6,520,180 B1 | 2/2003 | Sahmkow et al. | |
| 6,679,259 B2 | 1/2004 | Heesch | |
| 6,691,705 B2 | 2/2004 | Dittmann et al. | |

(Continued)

OTHER PUBLICATIONS

Cordero, L. et al., "The high-frequency pneumatic flow interrupter: Effects of different ventilatory strategies." Respiratory Care: vol. 37, No. 4. 1992. pp. 348-256.

*Primary Examiner* — Lynne Anderson
(74) *Attorney, Agent, or Firm* — McDermott Will & Emery LLP

(57) ABSTRACT

A method and system for controlling fluid flow settings by receiving a precondition pressure wave function, representative of a precondition frequency, a precondition amplitude and a precondition pressure of the fluid flow in the system, establishing an operating pressure wave function, representative of an operating frequency, an operating amplitude and an operating pressure of the fluid flow desired in the system, determining cycle error between the precondition pressure wave function and the operating pressure wave function, converting the cycle error to flow adjustment, and updating an operating flow with the flow adjustment.

28 Claims, 7 Drawing Sheets

ADAPTIVE HIGH FREQUENCY FLOW INTERRUPTER CONTROL SYSTEM DIAGRAM

(56) References Cited

U.S. PATENT DOCUMENTS

| | | |
|---|---|---|
| 6,729,343 B2 | 5/2004 | Ludwig et al. |
| 6,739,336 B1 | 5/2004 | Jalde et al. |
| 6,820,613 B2 | 11/2004 | Wenkebach et al. |
| 6,929,006 B2 | 8/2005 | Kruger et al. |
| 6,990,979 B2 | 1/2006 | Koch |
| 2005/0103338 A1 | 5/2005 | Bunke et al. |
| 2005/0133033 A1 | 6/2005 | Kruger et al. |

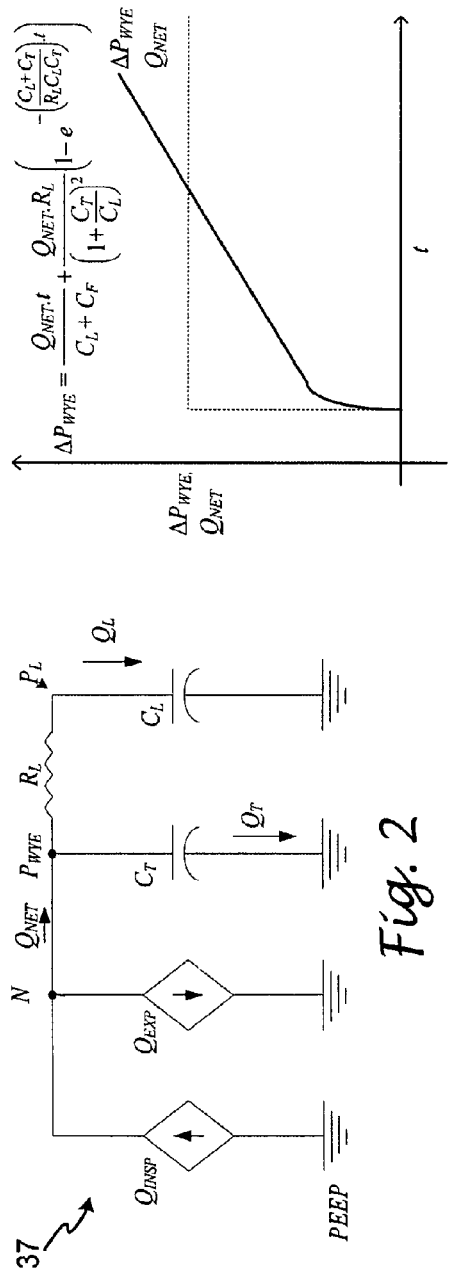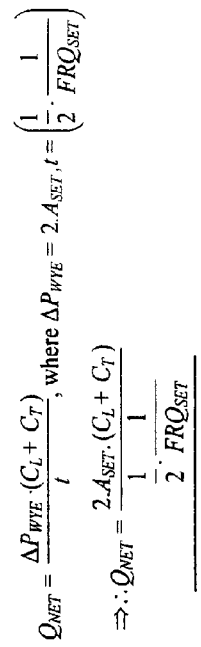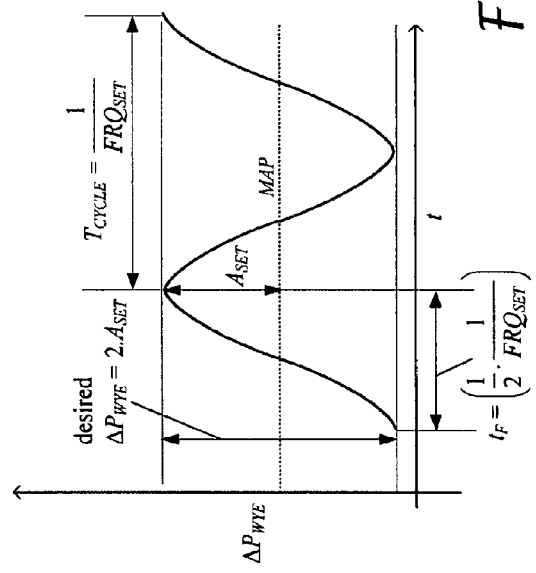
Fig. 2
Fig. 3
Fig. 4

SYSTEM AND METHOD FOR ADAPTIVE HIGH FREQUENCY FLOW INTERRUPTER CONTROL IN A PATIENT RESPIRATORY VENTILATOR

BACKGROUND OF THE INVENTION

1. Field of the Invention

The invention relates generally to a respiratory ventilator system. More particularly, the invention relates to a system and method for adaptive high frequency flow interrupter control in a respiratory ventilator system.

2. Description of Related Art

Conventional Mechanical Ventilators (CMV) are commonly used to provide breathing gas to hospital patients. These ventilators can be programmed to control the flow of the breathing gas inhaled and exhaled by the patient. The ventilation operating frequency used for CMV can range from 1-150 BPM, and the tidal volume can range from 4-20 ml/kg.

The breathing gas supplied to patients can be Oxygen, Air, Nitrox or Heliox. Nitrox is a breathing gas consisting of Oxygen ($O_2$) and Nitrogen ($N_2$) that is similar to air, but with a higher proportion of Oxygen than the normal 20.9%. Heliox is a breathing gas that is composed of a mixture of Helium (He) and Oxygen ($O_2$). Since Helium is less dense than Nitrogen, airway resistance is reduced due to the lower density of the inspired gas. This means that when one breathes Heliox, airway resistance is less, and therefore the mechanical energy required to ventilate the lungs, or the Work of Breathing (WOB) is decreased.

One type of respiratory ventilators commonly used for critically ill or neonatal patients is a High Frequency Ventilator (HFV). The HFV utilizes a ventilation technique that delivers very small tidal volumes at a high rate that exceeds the rate of normal breathing. The delivered small tidal volume is usually less than or equal to anatomical dead space volume. The frequency can range from 2.5-15 Hz, preferably no less than 150 Breaths Per Minute (BPM), and the low tidal volume can range from 0.5-5 ml/kg.

A High Frequency Flow Interrupter (HFFI) is a unique subset of an HFV system, where tidal volumes are delivered at high frequencies by "interruption" of delivered flow. HFFIs can be adapted from CMVs, with both conventional and high-frequency options combined. To produce high-frequency breaths, a flow of gas is interrupted by a valve mechanism that may be controlled pneumatically, mechanically or electronically by a microprocessor. Operator-selected parameters typically include mean airway pressure, amplitude pressure, and frequency, which is usually set between 2.5 and 15 Hz.

One HFFI system developed by Infrasonics is Infant Star 950, which "interrupts" the delivered flow by using electronically controlled solenoids to cause pressure pulses. This system utilizes an "open-loop" approach, which requires a clinician to select appropriate settings of mean pressure, frequency and amplitude. The pressure waveform can be manipulated by a series of pneumatic valves. Hence, for example, if the clinician determines that the initial settings were too high for the patient to tolerate or the patient dynamics has changed, the clinician would need to adjust the settings so that a comfortable setting is achieved. To ascertain a comfortable setting for the patient, an iterative manual process is required. This process is often left for the clinician who may not be at the patient bedside as conditions change. Furthermore, the process is prone to inaccuracies and errors.

With an increasing demand for improved HFFIs, there remains a continuing need in the art for an adaptive HFFI system that can provide consistent ventilation performance by automatically compensating for changes in patient dynamics and pressure regulation requirements.

SUMMARY OF THE INVENTION

A method and system for adaptive high frequency flow interrupter control is provided by receiving a precondition breathing gas pressure wave function, representative of a precondition frequency, a precondition amplitude and a precondition breathing gas pressure in the system, establishing an operating pressure wave function, representative of an operating frequency, an operating amplitude and an operating pressure desired in the system, determining cycle error between the precondition breathing gas pressure wave function and the operating pressure wave function, converting the cycle error to flow adjustment, and updating an operating flow with the flow adjustment.

One embodiment of the invention includes a system with a sample delay unit for establishing a one cycle delay that provides a relative flow adjustment between one cycle and another.

Another embodiment of the invention includes a system with a flow adjustment rate limiter for providing a smooth transition between the fluid flow and the operating flow.

A further embodiment of the invention includes a system that establishes a feed-forward flow from the operating frequency and the operating amplitude, and adds the feed-forward flow to the flow adjustment for updating the operating flow.

Yet another embodiment of the invention includes a cycle error measurement unit for determining an overshoot of the precondition breathing gas pressure wave function past the operating pressure wave function, an undershoot of the precondition breathing gas pressure wave function past the operating pressure wave function, and an error at peak between the operating pressure wave function and the precondition breathing gas pressure wave function.

Yet a further embodiment of the invention combines a conventional mechanical ventilator with the adaptive high frequency flow interrupter control system in the patient respiratory ventilator, such that a clinician can easily switch from one to the other.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein:

FIG. 2 illustrates an electric circuit diagram of a patient respiratory circuit with a patient receiving mechanical ventilation, according to an embodiment of the invention.

FIG. 3 illustrates a step diagram for the net flow rate and the equivalent change in patient airway pressure over time as a function of circuit/lung compliance and airway resistance, according to an embodiment of the invention.

FIG. 4 illustrates a desired sinusoidal graph for a patient airway pressure, according to an embodiment of the invention.

DETAILED DESCRIPTION OF THE PREFERRED EMBODIMENTS

Figure 1:
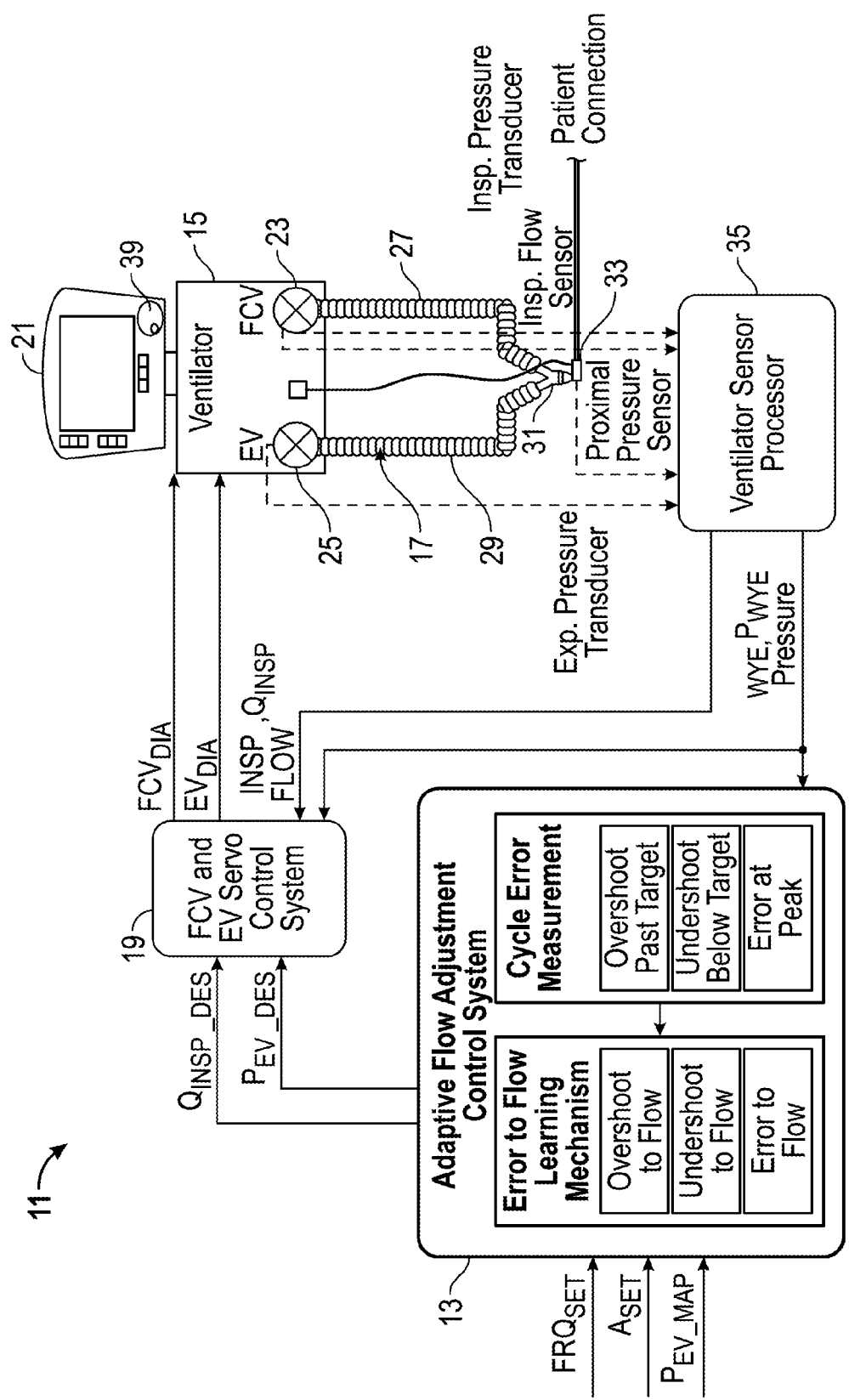
FIG. 1 illustrates a patient respiratory ventilation system incorporating an adaptive flow adjustment system, according to an embodiment of the invention.

FIG. 1 illustrates a patient respiratory ventilation system 11 incorporating an adaptive high frequency flow interrupter control system 13, according to one embodiment of the present invention. As shown in FIG. 1, the ventilation system 11 includes a ventilator 15, a patient circuit 17, an Adaptive High Frequency Flow Interrupter (AHFFI) control system 13, and a servo control subsystem 19.

The patient circuit 17 allows the circulation of inspiratory and expiratory gases between the ventilator 15 and a patient (not shown). The servo control system 19 controls the operations of the ventilator 15. For example, the ventilator 15 can have a Flow Control Valve (FCV) and an Exhalation Valve (EV) each with associated drive electronics for controlling inspiratory flow and airway pressure, respectively. The servo control system 19 can include a digital to analog converter that outputs analog signals $FCV_{D/A}$ and $EV_{D/A}$ to the respective drive electronics in ventilator 15.

The ventilator 15 preferably includes a user interface such as a monitor 21 for displaying various conditions and parameters of the patient and the ventilation system 11, and an input device 39, allowing the clinician or user to input the required settings and parameters. The input device may include buttons or any adjusting devices built on the front panel or other devices including keyboard, mouse or remote controls allowing the user to input setup information to the ventilator 15. Alternatively, the monitor 21 may be in the form of a touch screen in which both the display and input device are integrated. Based on the input data or information, the processor is operative to control the ventilator 15 for performing the desired operations.

The ventilator 15 further includes an inspiratory port 23 and an expiratory port 25 through which the inspiratory and expiratory gases are supplied and received to and from the patient through the patient circuit 17, respectively. An inspiratory Flow Control Valve (FCV) is typically installed at the inspiratory port 23 for controlling the inspiratory flow $Q_{INSP}$, and an Exhalation Valve (EV) is preferably installed at the expiratory port 25 for controlling the open/close condition of the expiratory port 25. Similarly, inspiratory and expiratory flow sensors can be installed at the inspiratory and expiratory ports 23 and 25 for measuring the inspiratory $Q_{INSP}$ and expiratory flow $Q_{EXP}$, respectively. Inspiratory and expiratory pressure transducers (not shown) may also be installed at the inspiratory and expiratory ports 23 and 25 for measuring the inspiratory and expiratory pressure $P_{INSP}$ and $P_{EXP}$, respectively.

As shown in FIG. 1, the patient circuit 17 can be a Y circuit that is used to connect the ventilator 15 to the patient (not shown). The patient circuit 17 includes an inspiratory limb 27 with one end coupled to the inspiratory port 23 and an expiratory limb 29 with one end coupled to the expiratory port 25 of the ventilator 15. The other ends of the inspiratory limb 27 and the expiratory limb 29 are coupled to a breathing piece 31 that is applied to the patient via an endotracheal tube (not shown). Other accessories or component devices such as filters may also be installed in various parts of the patient circuit 17. To directly measure the gas flow $Q_{WYE}$ delivered to the patient, a flow sensor 33 is preferably installed at the breathing piece 31. It will be appreciated that the inspiratory and expiratory flow sensors and the inspiratory and expiratory pressure transducers may also be installed near the inspiratory port 23 and expiratory port 25, respectively. A proximal pressure transducer (not shown) can also be installed at the breathing piece 31 to determine the WYE pressure $P_{WYE}$ measured at the breathing piece 31.

The measurable process variables, including the inspiratory flow $Q_{INSP}$, the inspiratory pressure $P_{INSP}$, the expiratory pressure $P_{EXP}$ and the pressure $P_{WYE}$ measured at the breathing piece 31 are sampled at a predetermined frequency. For example, in one embodiment, these processes are sampled every cycle (2 msec). The ventilator 15 may include a ventilator sensor processing unit 35 operative to process the measured parameters, including $Q_{INSP}$, $P_{INSP}$, $P_{EXP}$, $P_{WYE}$ and other sensor readings before outputting to the Adaptive High Frequency Flow Interrupter (AHFFI) control system 13 and the servo control system 19.

The AHFFI control system 13 regulates the airway pressure for given user settings. The AHFFI control system 13 is a closed-loop adaptive control approach that modulates an operating inspiratory flow target based on "errors" measured during the last breath cycle. This AHFFI system 13 can be designed to deliver volumes at high frequencies (150<BPM≤900 or 2.5-1.5 Hz). In one embodiment, the AHFFI control system 13 can be a closed control loop that integrates the FCV and EV servo control system 19.

The adaptive control approach utilizes the measured $P_{WYE}$ in a priority rule-based or optimization algorithm that can be executed at the beginning of every cycle for the set operating mean airway pressure $P_{EV\_MAP}$, operating frequency $FRQ_{SET}$, and operating amplitude $A_{SET}$. Based on algorithmic calculations, the AHFFI control system 13 outputs, to the servo control system 19, a final exhalation pressure servo operating target $P_{EV\_DES}$ and an updated final inspiratory operating flow servo target $Q_{INSP\_DES}$. This process is repeated at the beginning of every breath cycle as the inspiratory flow target for the FCV and EV servo control system 19 adapts to the current patient conditions for the given user-selected settings. Also, during every sample (2 ms), the AHFFI control system 13 updates a final exhalation pressure servo operating target $P_{EV\_DES}$ in accordance to the user-selected settings.

FIG. 2 illustrates an electric circuit diagram 37 of a patient respiratory circuit with a patient receiving mechanical ventilation, according to an embodiment of the invention. In a patient respiratory circuit, the gas flow Q circulates from a high pressure level to a low pressure level in a way similar to the electric current I. The gas flow Q through a circuit element such as an airway resistance causes a pressure drop ΔP similar to the voltage drop ΔV in the electric circuit 37.

As shown in FIG. 2, the patient respiratory circuit typically comprises a patient circuit for circulating gas between a ventilator and a patient. The ventilator is operative to provide an inspiratory gas flow $Q_{INSP}$ and receive an expiratory gas flow $Q_{EXP}$ to and from the patient through the patient circuit, respectively. Ideally, the flow differential between the inspiratory flow $Q_{INSP}$ and the expiratory flow $Q_{EXP}$, that is, the net flow $Q_{NET}$, is all to be delivered to the patient, so as to provide the tidal volume required thereby. However, in real practice, the volume loss within the patient circuit is inevitable due to the circuit compliance $C_T$ thereof. The circuit compliance $C_T$ is in parallel flow communication with the lung compliance $C_L$ and behaves similarly to a capacitor in the electric circuit 37.

The circuit compliance $C_T$ is defined as a ratio of the volume offset by the patient circuit to the pressure across the patient circuit. The offset volume is proportional to the circuit compliance $C_T$. The lung compliance $C_L$ is similarly defined as the ratio of the volume offset by the patient lung to the pressure across the lung. Therefore, when the circuit compliance $C_T$ is much larger than the lung compliance $C_L$, a majority of the net flow $Q_{NET}$ will be distributed to the patient circuit instead of being supplied to the patient's lung.

As shown in FIG. 2, the ground level for the patient respiratory circuit is referred to as Positive End Expiratory Pressure (PEEP). Therefore, the pressure across the patient circuit is thus the pressure differential between the airway pressure measured at a breathing piece 31 of the patient circuit $P_{WYE}$ and PEEP. An airway resistance $R_L$ exists in the patient's airway, such that the pressure applied to the patient's lung $P_L$ will be reduced by a factor of $Q_L^2 R_L$. The airway pressure at the patient circuit $P_{WYE}$ and the lung pressure $P_L$ can be expressed by the following equation:

$$P_{WYE} = P_L + Q_L^2 R_L \quad (1).$$

By definition, the circuit compliance $C_T$ and the lung compliance $C_L$ can be expressed as:

$$C_T = \frac{V_{TID}}{P_{WYE} - PEEP}. \quad (2)$$

$$C_L = \frac{V_{TID}}{P_L - PEEP}. \quad (3)$$

The tidal volume $V_{TID}$ is the actual gas volume delivered to the lung of the patient, and $V_{CC}$ is the gas volume offset by the circuit compliance $C_T$. The gas volumes $V_{TID}$ and $V_{CC}$ can be derived by integrating the gas flow rate $Q_T$ and $Q_L$ through the patient circuit and the patient's lung.

When we consider the response of the patient airway pressure $P_{WYE}$ due to a step input of a given net flow $Q_{NET}$, the change in patient airway pressure over time as a function of circuit/lung compliance and airway resistance can be expressed as:

$$\Delta P_{WYE} = \underbrace{\frac{Q_{NET} \cdot t}{C_L + C_T}}_{\text{steady-state}} + \underbrace{\frac{Q_{NET} \cdot R_L}{\left(1 + \frac{C_T}{C_L}\right)^2}\left(1 - e^{-\left(\frac{C_L + C_T}{R_L C_L C_T}\right)t}\right)}_{\text{dynamic}}. \quad (4)$$

FIG. 3 graphically illustrates the change in patient airway pressure $\Delta P_{WYE}$ over time due to a step net flow rate $Q_{NET}$, according to one embodiment of the invention. The plotted $\Delta P_{WYE}$ values are determined from Equation (4).

FIG. 4 illustrates a desired graph for a patient airway pressure $\Delta P_{WYE}$, according to an embodiment of the invention. The graph shows a sinusoidal wave; however, it is understood by a person skilled in the art that other wave functions can be used, such as, but not limited to, a square wave or a triangular wave function. Since a clinician selects the operating frequency $FRQ_{SET}$ and operating amplitude $A_{SET}$, which dictates the desired change in airway pressure and the time at which it must occur, the minimum required net flow can be easily solved for while neglecting airway resistance (i.e. the dynamic term in Equation (4) is ignored). Therefore, the change in patient airway pressure $\Delta P_{WYE}$ over time as a function of circuit/lung compliance can be reduced to:

$$\Delta P_{WYE} = \frac{Q_{NET} \cdot t}{C_L + C_T}. \quad (5)$$

Rearranging Equation (5), the net operating flow $Q_{NET}$ can be expressed as:

$$Q_{NET} = \frac{\Delta P_{WYE} \cdot (C_L + C_T)}{t}. \quad (6)$$

The desired change in patient airway pressure $\Delta P_{WYE}$ as a function of operating amplitude $A_{SET}$, is:

$$\Delta P_{WYE} = 2 \cdot A_{SET} \quad (7).$$

Therefore, substituting Equation (7) in Equation (6), the net operating flow $Q_{NET}$ expressed as a function of operating frequency $FRQ_{SET}$ and operating amplitude $A_{SET}$, where $$t = \left(\frac{1}{2} \cdot \frac{1}{FRQ_{SET}}\right)$$

is:

$$Q_{NET} = \frac{2 \cdot A_{SET} \cdot (C_L + C_T)}{\frac{1}{2} \cdot \frac{1}{FRQ_{SET}}}. \quad (8)$$

While Equation (8) ignores the effect of patient airway resistance, it does illustrate that the minimum operating net flow required is a function of the patient compliance $C_L$, circuit compliance $C_T$ and user selected operating frequency $FRQ_{SET}$ and operating amplitude $A_{SET}$.

If all conditions are known, the delivered operating flow can be set accordingly, however as patient conditions or user settings change, the flow must be adjusted to achieve a desirable system operation. If the necessary flow is not adjusted, poor airway pressure regulation and inadequate patient ventilation occurs. To account for changing patient conditions the clinician is often left with the cumbersome task of manually adjusting the settings. However, the clinician may not be at the patient bedside as conditions change. According to the present invention, the AHFFI control system 13 provides an automated control approach that adaptively adjusts to the minimum operating flow required to compensate for changes in patient conditions while meeting the desired pressure regulation requirements.

Figure 5:
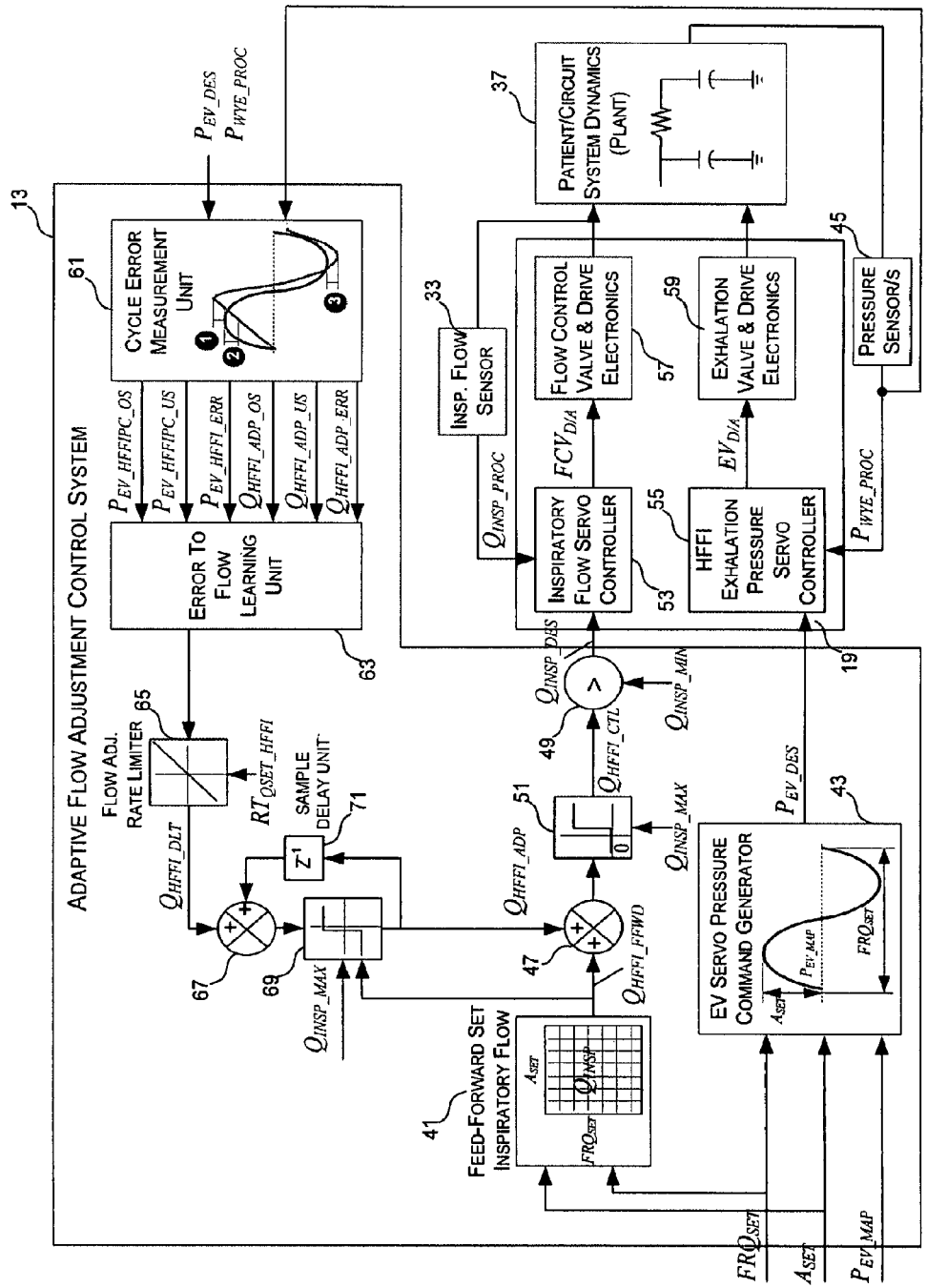
FIG. 5 illustrates an adaptive high frequency flow interrupter control system diagram incorporating a servo control system, according to an embodiment of the invention.

FIG. 5 illustrates an Adaptive High Frequency Flow Interrupter (AHFFI) control system diagram 13, according to an embodiment of the invention. As shown in FIG. 5, the AHFFI control system 13 can be integrated with the servo control system 19, a pressure sensor 45, an inspiratory flow sensor 33, and patient/circuit system dynamics 37.

The servo control system 19 includes an inspiratory flow servo controller 53 and an HFFI Exhalation pressure servo controller 55. The inspiratory flow servo controller 53 is coupled to a flow control valve & drive electronics 57, while the HFFI Exhalation pressure servo controller 55 is coupled to an exhalation valve & drive electronics 59. The inspiratory flow servo controller 53 utilizes the inspiratory flow sensor 33 as feedback and regulates inspiratory flow to a given flow command. The HFFI Exhalation pressure servo controller 55 utilizes the pressure sensor 45 as feedback and regulates airway pressure (or WYE pressure) to a given pressure command.

Coupled to the servo control system 19 is the patient/circuit system dynamics 37 which represents the patient dynamics or control system plant to be controlled. Because the patient/circuit system dynamics 37 has a wide range of operating conditions that are cumbersome for a clinician to resolve, the need for an adaptive control approach is necessary. The inspiratory flow sensor 33 and the pressure sensor 45 are coupled to the servo control system 19 to provide a measurement of the inspiratory flow $Q_{INSP\_PROC}$ and an estimate or direct measurement of the patient WYE pressure $P_{WYE\_PROC}$, respectively. The patient precondition WYE pressure $P_{WYE\_PROC}$ can be determined using the following expression:

$$P_{WYE\_PROC} = \begin{cases} (P_{INSP\_PROC} + P_{EXP\_PROC})/2. & (9) \\ P_{PRX\_PROC}. & (10) \end{cases}$$

Equation (9) is preferably used if there is no proximal pressure transducer used, where $P_{EXP\_PROC}$ and $P_{INSP\_PROC}$ are the measured expiratory and inspiratory pressures, respectively, while Equation (10) is preferably used if a proximal pressure transducer is utilized which would provide a direct measurement of the patient WYE pressure $P_{PRX\_PROC}$.

The AHFFI control system 13 includes an EV servo pressure command generator 43, which develops a certain command profile depending on a given operating frequency $FRQ_{SET}$, operating amplitude $A_{SET}$, and operating mean airway pressure $P_{EV\_MAP}$. The frequency $FRQ_{SET}$ is preferably in the range of 2.5-15 Hz. For frequencies greater than 5 Hz, the maximum value assigned to the amplitude $A_{SET}$ is 20 cmH$_2$O, according to one embodiment. The mean airway pressure $P_{EV\_MAP}$ should be at least equal to the operating amplitude $A_{SET}$, since the system is incapable of regulating to negative airway pressures. The command generator 43 displays a sinusoidal wave in FIG. 5; however, other wave functions can be used, such as, but not limited to, a square wave or a triangular wave function. The command generator 43 outputs a final HFFI exhalation operating servo target $P_{EV\_DES}$ to the HFFI Exhalation pressure servo controller 55.

Figure 6:
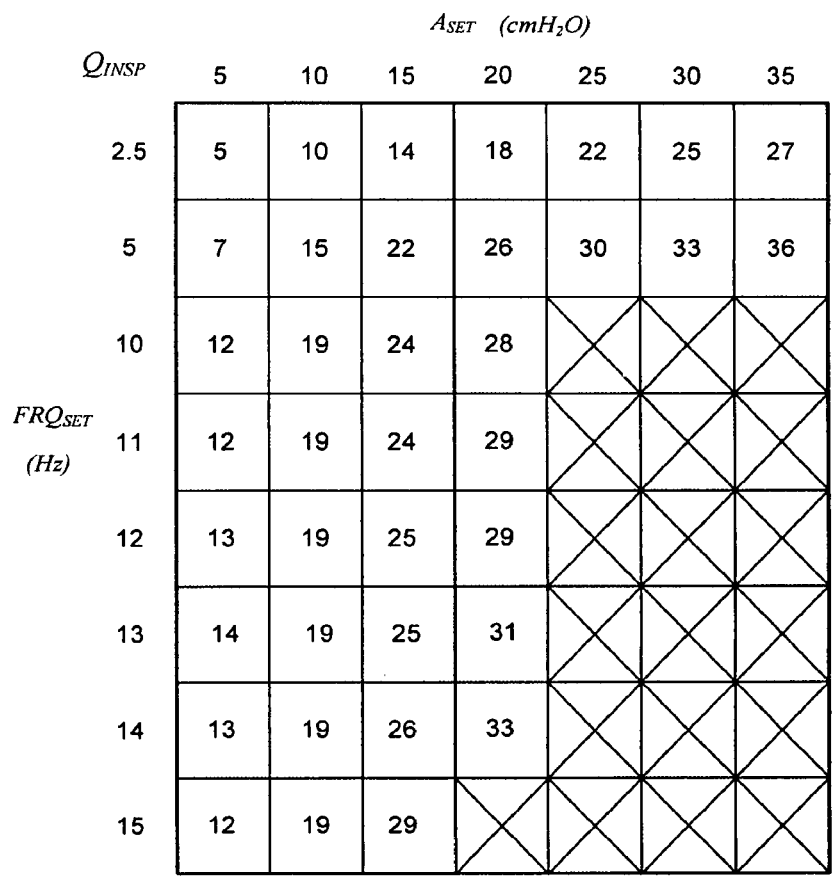
FIG. 6 illustrates a feed-forward inspiratory flow command calibration table, according to one embodiment of the invention.

In one embodiment, the AHFFI control system 13 also includes a feed-forward set inspiratory flow look-up table 41 as part of the AHFFI control scheme. Based on a set operating frequency $FRQ_{SET}$ and operating amplitude $A_{SET}$, an open-loop feed-forward estimated value for inspiratory flow $Q_{INSP}$ can be determined. FIG. 6 illustrates a feed-forward inspiratory flow command calibration table, according to one embodiment of the present invention. The calibration table provides an open-loop estimate of what initial inspiratory flow $Q_{INSP}$ to use. Based on the calibration table, an open-loop inspiratory flow $Q_{HFFI\_FFWD}$ commanded as a feed-forward term by the AHFFI control system is outputted to the adder 47.

In the AHFFI control scheme, an adder 47 combines the open-loop inspiratory flow adjustment $Q_{HFFI\_FFWD}$ with a closed-loop adaptive inspiratory flow $Q_{HFFI\_ADP}$ outputted from a limiter 69. The adder 47 outputs the combined flow to limiter 51, which limits the combined flow between a maximum allowable inspiratory operating flow command $Q_{INSP\_MAX}$ and zero flow. This limited AHFFI inspiratory flow servo target, $Q_{HFFI\_CTL}$, is outputted to comparator 49. The comparator 49 determines the greater flow demand between the inspiratory flow servo target $Q_{HFFI\_CTL}$ and the minimum user selected inspiratory operating flow $Q_{INSP\_MIN}$, and outputs the final inspiratory flow target $Q_{INSP\_DES}$ to the inspiratory flow servo controller 53.

The AHFFI control system 13 also includes a cycle error measurement unit 61, an error to flow learning unit 63, a flow adjustment rate limiter 65, an adder 67, a limiter 69, and a sample delay unit 71. In one embodiment, the sample delay unit 71 can provide a one cycle delay to the AHFFI control system 13. The flow adjustment rate limiter 65 can be used to provide a smooth transition between the measured flow rate and the corrected flow rate. The AHFFI control system 13 receives a preconditioned pressure $P_{WYE\_PROC}$ from the patient/circuit 37 and operating pressure $P_{EV\_DES}$ from the EV servo pressure command generator 43.

Unlike open-loop systems 52, the AHFFI control system 13, which implements a closed-loop scheme 54, provides airway pressure feedback that results in higher pressure regulation accuracy. The AHFFI control system 13 provides consistent pressure regulation by compensating for changes in patient compliance, airway resistance, amplitude and frequency settings. The closed-loop approach 54 also provides compensation for changes in actuator performance, system leaks, etc. unlike open-loop approaches 52. Furthermore, the AHFFI control system 13 optimizes the "minimum" flow required to achieve user-specified operation settings.

The cycle error measurement unit 61 compares the pressures $P_{WYE\_PROC}$ and $P_{EV\_DES}$ to determine the relative cycle error between the two pressures. The error to flow learning unit 63 receives the results from the cycle error measurement unit 61 and outputs it to the flow adjustment rate limiter 65. The flow adjustment rate limiter 65, receives the outputted results from the error to flow learning unit 63, and compares it to a maximum allowable delta inspiratory flow servo target correction $RT_{QSET\_HFFI}$, and outputs a computed delta inspiratory flow servo target correction $Q_{HFFI\_DLT}$, to the adder 67. The adder 67 combines the computed delta inspiratory flow servo target correction $Q_{HFFI\_DLT}$ with the flow result from the sample delay unit 71, preferably the flow result of a one cycle delay, and outputs it to a limiter 69. Limiter 69 also receives the maximum allowable inspiratory flow command $Q_{INSP\_MAX}$ and the open-loop inspiratory flow $Q_{HFFI\_FFWD}$, and outputs the closed-loop adaptive inspiratory flow adjustment $Q_{HFFI\_ADP}$ to adder 47.

Figure 7:
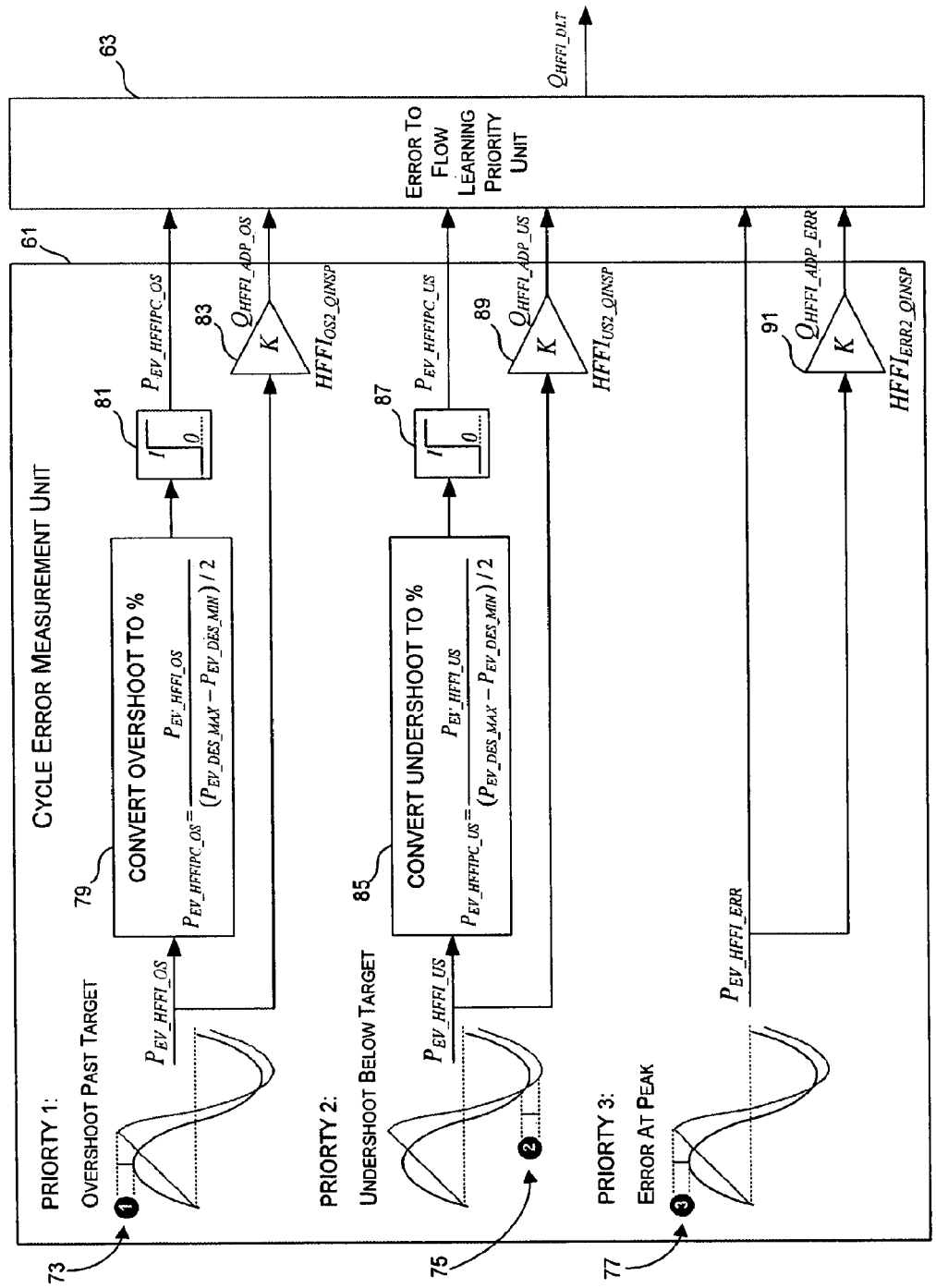
FIG. 7 illustrates a cycle error measurement system diagram incorporating an error to flow learning unit, according to an embodiment of the invention.

Referring to FIG. 7, the cycle error measurement unit 61 determines the overshoots or undershoots between the measured preconditioned airway pressure and the desired operating patient airway pressure. The cycle error measurement unit 61 measures the overshoot past target 73 (overshoot pressure $P_{EV\_HFFI\_OS}$ measured during the last cycle relative to the maximum AHFFI operating pressure target that is commanded), the undershoot below target 75 (undershoot pressure $P_{EV\_HFFI\_US}$ measured during the last cycle relative to the minimum AHFFI operating pressure target that is commanded), and the error at peak 77 (error pressure $P_{EV\_HFFI\_ERR}$ measured during the last cycle when the maximum AHFFI operating pressure target is commanded).

The overshoot past target 73 is converted by converter 79 to a measured percent pressure overshoot past the maximum AHFFI operating pressure target during the last cycle $P_{EV\_HFFIPC\_OS}$, and is limited by limiter 81 and amplified by amplifier 83. The converter 79 utilizes the following expression for conversion:

$$P_{EV\_HFFIPC\_OS} = \frac{P_{EV\_HFFI\_OS}}{(P_{EV\_DES\_MAX} - P_{EV\_DES\_MIN})/2}. \quad (11)$$

Similarly, undershoot below target 75 is converted by converter 85 to a measured percent pressure undershoot past the minimum AHFFI operating pressure target during the last cycle $P_{EV\_HFFIPC\_US}$ and is limited by limiter 87, and amplified by amplifier 89. The converter 85 utilizes the following expression for conversion:

$$P_{EV\_HFFIPC\_US} = \frac{P_{EV\_HFFI\_US}}{(P_{EV\_DES\_MAX} - P_{EV\_DES\_MIN})/2}. \quad (12)$$

The term $P_{EV\_DES\_MAX}$ is the maximum AHFFI operating pressure target during a given cycle, while the term $P_{EV\_DES\_MIN}$ is the minimum AHFFI operating pressure target during a given cycle.

The limiter 81 outputs the measured percent pressure overshoot $P_{EV\_HFFIPC\_OS}$ to the error to flow learning unit 63. The amplifier 83, with a gain $HFFI_{OS2\_QINSP}$, converts pressure overshoot to an adaptive delta inspiratory flow adjustment servo target correction $Q_{HFFI\_ADP\_OS}$. This adaptive delta inspiratory flow adjustment servo target correction $Q_{HFFI\_ADP\_OS}$ is outputted to the error to flow learning unit 63. Furthermore, the limiter 87 outputs the measured percent pressure overshoot $P_{EV\_HFFIPC\_US}$ to the error to flow learning unit 63. The amplifier 89, with a gain $HFFI_{US2\_QINSP}$, converts pressure undershoot to an adaptive delta inspiratory flow adjustment servo target correction $Q_{HFFI\_ADP\_US}$. This adaptive delta inspiratory flow adjustment servo target correction $Q_{HFFI\_ADP\_US}$ is outputted to the error to flow learning unit 63.

If there is an error at peak 77, the measured pressure error during the last cycle when the maximum AHFFI operating pressure target is commanded $P_{EV\_HFFI\_ERR}$ is outputted to the error to flow learning unit 63 and the amplifier 93. The amplifier 93, with a gain $HFFI_{ERR2\_QINSP}$, converts the measured pressure error $P_{EV\_HFFI\_ERR}$ to an adaptive delta inspiratory flow adjustment servo target correction $Q_{HFFI\_ADP\_ERR}$. This adaptive delta inspiratory flow adjustment servo target correction $Q_{HFFI\_ADP\_ERR}$ is outputted to the error to flow learning unit 63.

Figure 8:
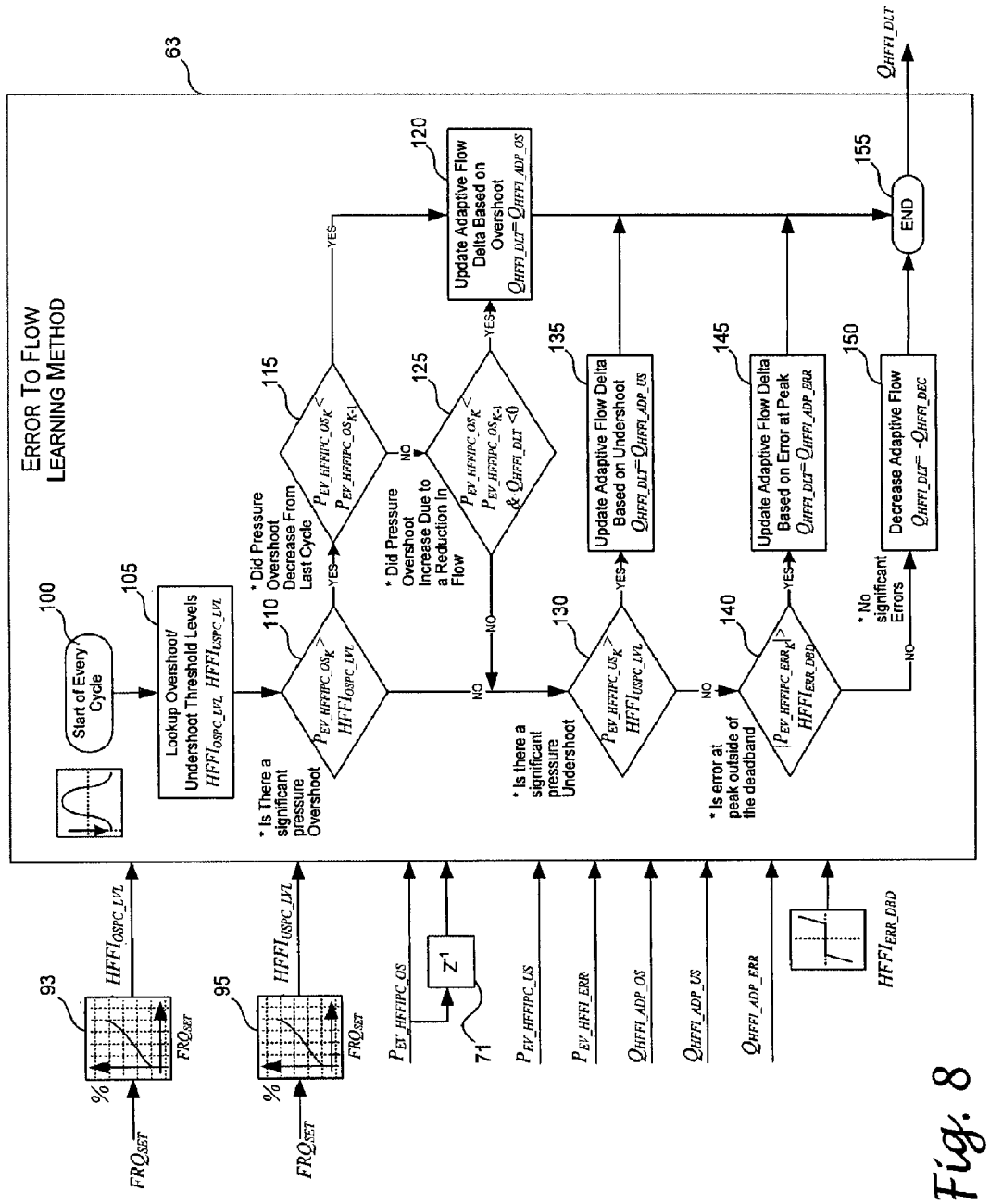
FIG. 8 is a flow chart of an error to flow learning method, according to an embodiment of the invention.

FIG. 8 is a flow chart of an error to flow learning method, according to an embodiment of the invention. The error to flow learning unit 63 receives the results from the cycle error measurement unit 61 and utilizes the exemplary flow chart to adjust the operating inspiratory flow. At the start of every cycle (100), the error to flow learning unit 63 determines the percent pressure overshoot and percent pressure undershoot threshold levels $HFFI_{OSPC\_LVL}$ and $HFFI_{USPC\_LVL}$, respectively (105). These values can be determined from calibration charts 93 and 95 that depend on the set frequency $FRQ_{SET}$.

The error to flow learning unit 63 first determines if there is a significant pressure overshoot by comparing the measured percent pressure overshoot past the maximum AHFFI operating pressure target $P_{EV\_HFFIPC\_OS_K}$ with the percent pressure overshoot threshold $HFFI_{OSPC\_LVL}$ used by the error to flow learning unit 63 during a given cycle. If $P_{EV\_HFFIPC\_OS_K}$ is greater than $HFFI_{OSPC\_LVL}$, then the error to flow learning unit 63 determines if the pressure overshoot decreased from the last cycle by comparing the measured percent pressure overshoot past the maximum AHFFI operating pressure target during a given cycle $P_{EV\_HFFIPC\_OS_K}$ with the measured percent pressure overshoot past the maximum AHFFI operating pressure target during the last cycle $P_{EV\_HFFIPC\_OS_{K-1}}$ (115). The measured percent pressure overshoot during the last cycle $P_{EV\_HFFIPC\_OS_{K-1}}$ can be attained by using the sample delay unit 71.

If the pressure overshoot decreased from the last cycle, then the error to flow learning unit 63 updates the adaptive flow delta based on the overshoot by setting $Q_{HFFI\_DLT} = Q_{HFFI\_ADP\_OS}$ (120). If the pressure overshoot increased from the last cycle, then the error to flow learning unit 63 determines if the pressure overshoot increase was due to a reduction in flow (125) by using the following relation:

$$P_{EV\_HFFIPC\_OS_K} > P_{EV\_HFFIPC\_OS_{K-1}} \& Q_{HFFI\_DLT} < 0 \quad (13)$$

If the pressure overshoot increased due to a reduction in flow, then the error to flow learning unit 63 updates the adaptive flow delta based on the overshoot by setting $Q_{HFFI\_DLT} = Q_{HFFI\_ADP\_OS}$ (120). However, if the pressure overshoot increase was not due to a reduction in flow, then the error to flow learning unit 63 determines if there is a significant pressure undershoot by comparing the measured percent pressure undershoot past the minimum HFFI pressure target $P_{EV\_HFFIPC\_US_K}$ with the percent pressure undershoot threshold used by the adaptive HFFI control system during a given cycle $HFFI_{USPC\_LVL}$ (130). Similarly, if there is no pressure overshoot, where $P_{EV\_HFFIPC\_OS_K}$ is less than $HFFI_{OSPC\_LVL}$, then the error to flow learning unit 63 determines if there is a significant pressure undershoot.

If $P_{EV\_HFFIPC\_US_K}$ is greater than $HFFI_{USPC\_LVL}$, then the error to flow learning unit 63 updates the adaptive flow delta based on the undershoot by setting $Q_{HFFI\_DLT} = Q_{HFFI\_ADP\_US}$ (135). However, if there is no significant pressure undershoot, the error to flow learning unit 63 determines if the error at peak is outside the dead-band (140) by using the following relation:

$$|P_{EV\_HFFI\_ERR_K}| > HFFI_{ERR\_DBD} \quad (14).$$

If the relation in Equation (14) is satisfied, then the error to flow learning unit 63 updates the adaptive flow delta based on the error at peak by setting $Q_{HFFI\_DLT} = Q_{HFFI\_ADP\_ERR}$ (145). However, if the error at the peak is within the dead-band, then there are no significant errors and the error to flow learning unit 63 decreases the flow by setting $Q_{HFFI\_DLT} = -Q_{HFFI\_DEC}$ (150). The term $Q_{HFFI\_DEC}$ is the delta inspiratory flow servo target reduction during adaptation when no significant errors exist.

Once the adaptive flow is updated (120), (135), (145) and (150), the error to flow learning unit 63, completes the process and outputs the computed delta inspiratory flow servo target correction $Q_{HFFI\_DLT}$ to the flow adjustment rate limiter 65 (155).

Figure 9:
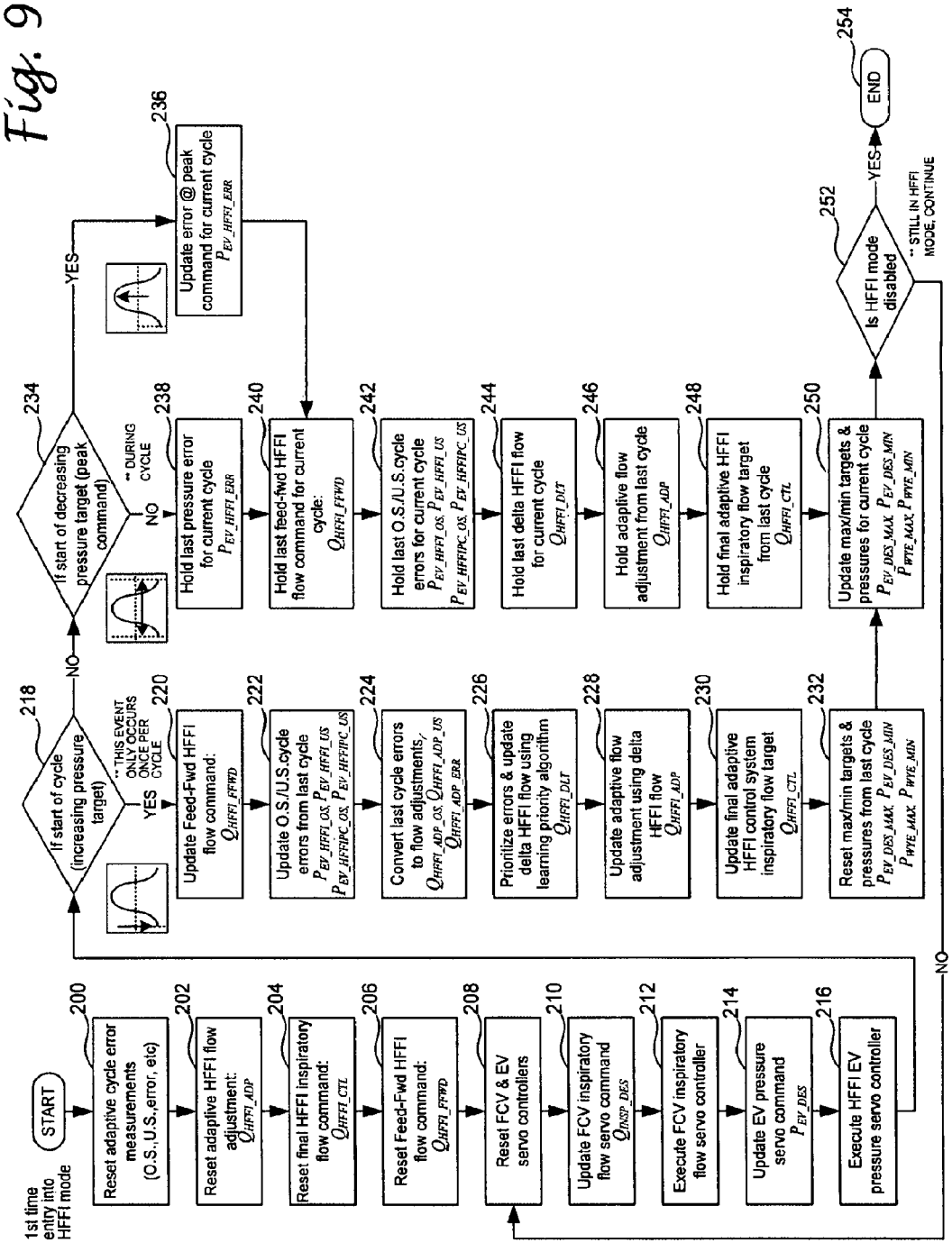
FIG. 9 is a flow chart illustrating a method for operating an adaptive high frequency flow interrupter control system, according to an embodiment of the invention.

FIG. 9 is a flow chart illustrating a method for operating an AHFFI control system 13, according to an embodiment of the invention. Preferably, the AHFFI control system 13 can be combined with a Conventional Mechanical Ventilator (CMV) in a patient respiratory ventilation system 11, such that a clinician can switch from a CMV control mode to an AHFFI control mode.

Initially, the AHFFI control system 13 resets the adaptive cycle error measurements, the captured minimum/maximum AHFFI operating pressure targets, and the minimum/maximum measured WYE pressures upon entry into HFFI control mode as follows (200):

$$P_{EV\_DES\_MAX_{K-1}} = 0$$

$$P_{EV\_DES\_MIN_{K-1}} = P_{EV\_DES_K}$$

$$P_{WYE\_MAX_{K-1}} = 0$$

$$P_{WYE\_MIN_{K-1}} = P_{WYE\_PROC_K}$$

$$P_{EV\_HFFI\_OS_{K-1}} = 0$$

$$P_{EV\_HFFI\_US_{K-1}} = 0$$

$$P_{EV\_HFFI\_ERR_{K-1}} = 0$$

$$P_{EV\_HFFIPC\_OS_{K-1}} = 0$$

$$P_{EV\_HFFIPC\_US_{K-1}} = 0 \quad (15).$$

These initial conditions, expressed in Equation (15), are set accordingly to ensure proper functioning of the AHFFI control system 13. Preferably, these initial conditions are set if the patient respiratory ventilation system 11 is switched from the CMV control mode to an AHFFI control mode 13, thereby resetting any preconditioned pressure measurements.

Next, the AHFFI control system 13 resets the last computed closed-loop adaptive inspiratory flow adjustment target correction $Q_{HIFF\_ADP_{K-1}} = 0$ (202), the final adaptive inspiratory operating flow servo target $Q_{HFFI\_CTL_{K-1}} = 0$ (204), the feed-forward inspiratory flow servo target $Q_{HFFI\_FFWD_{K-1}} = 0$ (206), and the FCV and EV servo controllers 53 and 55 (208).

The AHFFI control system 13 then updates the FCV inspiratory operating flow servo command $Q_{INSP\_DES_K}$ (210). The inspiratory operating flow servo command uses a one-cycle delay of what the AHFFI control system 13 provides as a flow adaptation. This inspiratory flow servo command is the greater flow demand between the user-selected minimum inspiratory flow $Q_{INSP\_MIN_K}$ and the final AHFFI operating inspiratory flow target from the last cycle $Q_{HFFI\_CTL_{K-1}}$:

$$Q_{INSP\_DES_K} = \max(Q_{INSP\_MIN_K}, Q_{HFFI\_CTL_{K-1}}) \quad (16).$$

The user-selected minimum inspiratory flow $Q_{INSP\_MIN_K}$ is used to specify a minimum flow allowable that would ensure safe operation of the patient respiratory ventilation system 11. For example, the patient respiratory ventilation system 11 can have heated wires for a humidifier, and these heated wires need a given amount of flow to ensure that they do not melt the endotracheal tubing. To prevent meltdown, the user-selected minimum inspiratory flow $Q_{INSP\_MIN_K}$ is preferably at least one liter per minute.

Once the flow servo command is updated, the FCV inspiratory flow servo controller 53 is executed (212).

The AHFFI control system 13 also updates the EV operating pressure servo command $P_{EV\_DES_K}$ (214). Depending on a given operating frequency $FRQ_{SET}$, operating amplitude $A_{SET}$, and operating mean airway pressure $P_{EV\_MAP}$, the EV servo pressure command generator 43 would develop a corresponding wave function. The command generator 43 displays a sinusoidal wave in FIG. 5; however, other wave functions can be used, such as, but not limited to, a square wave or a triangular wave. The sinusoidal wave has at least an offset equal to the user-selected amplitude $A_{SET}$, since negative pressures cannot be regulated, such that the operating pressure servo command is expressed by the following function:

$$P_{EV\_DES_K} = A_{SET\,K} * \sin(2 \cdot \pi \cdot FRQ_{SET\,K}) + \max(P_{EV\_MAP_K}, A_{SET\,K}) \quad (17).$$

Once the EV pressure servo command is updated, the HFFI Exhalation pressure servo controller 55 is executed (216).

Next, the AHFFI control system 13 determines, preferably once every cycle, if it is operating at a start of a cycle (218). The AHFFI control system is operating at a start of a cycle at the first instance where there is an increasing pressure command.

If the AHFFI control system 13 is operating at a start of a cycle, then the feed-forward inspiratory flow command is updated (220). At the start of every cycle (i.e. start of increasing pressure command), the feed-forward inspiratory flow command can be determined, from the calibration table of FIG. 6, based on the user-selected frequency $FRQ_{SET}$ and amplitude $A_{SET}$, as shown in the following expression:

$$Q_{HFFI\_FFWD_K} = f(FRQ_{SET}, A_{SET}) \quad (18).$$

Next, the AHFFI control system 13, operating at a start of a cycle, updates the overshoot 73 and undershoot 75 cycle errors from the last cycle (222). The measured pressure overshoot $P_{EV\_HFFI\_OS_K}$ and undershoot $P_{EV\_HFFI\_US_K}$ past the AHFFI operating pressure target captured during the last cycle can be determined using the following expressions:

$$P_{EV\_HFFI\_OS_K} = \max(0, (P_{WYE\_MAX_{K-1}} - P_{EV\_DES\_MAX_{K-1}})) \quad (19).$$

$$P_{EV\_HFFI\_US_K} = \max(0, (P_{EV\_DES\_MIN_{K-1}} - P_{WYE\_MIN_{K-1}})) \quad (20).$$

The measured percent pressure overshoot and undershoot past the AHFFI operating pressure target during the last cycle can also be determined using the following expressions:

$$P_{EV\_HFFIPC\_OS_K} = \max\left(0, \left(\frac{2 * P_{EV\_HFFI\_OS_K}}{P_{EV\_DES\_MAX_{K-1}} - P_{EV\_DES\_MIN_{K-1}}}\right)\right). \quad (21)$$

$$P_{EV\_HFFIPC\_OS_K} = \min(P_{EV\_HFFIPC\_OS_K}, 1). \quad (22)$$

$$P_{EV\_HFFIPC\_US_K} = \max\left(0, \left(\frac{2 * P_{EV\_HFFI\_US_K}}{P_{EV\_DES\_MAX_{K-1}} - P_{EV\_DES\_MIN_{K-1}}}\right)\right). \quad (23)$$

$$P_{EV\_HFFIPC\_US_K} = \min(P_{EV\_HFFIPS\_US_K}, 1). \quad (24)$$

Next, the AHFFI control system 13, operating at a start of a cycle, converts the last cycle errors to flow adjustments (224). The delta inspiratory flow adjustment servo target correction to compensate for pressure overshoot $Q_{HFFI\_ADP\_OS_K}$ and undershoot $Q_{HFFI\_ADP\_US_K}$ can be determined using the following expressions:

$$Q_{HFFI\_ADP\_OS_K} = HFFI_{OS2\_QINSP} * P_{EV\_HFFI\_OS_K} \quad (25).$$

$$Q_{HFFI\_ADP\_US_K} = HFFI_{US2\_QINSP} * P_{EV\_HFFI\_US_K} \quad (26).$$

The delta inspiratory flow adjustment to compensate for the pressure error captured when the peak operating pressure target is commanded can be determined using the following expression:

$$Q_{HFFI\_ADP\_ERR_K} = HFFI_{ERR2\_QINSP} * P_{EV\_HFFI\_ERR_K} \quad (27).$$

Upon converting the last cycle errors to flow adjustments, the AHFFI control system 13 prioritizes errors to make a final adaptive flow adjustment and updates the delta HFFI flow $Q_{HFFI\_DLT}$ as described earlier using the error to flow priority learning unit 63 (226). As shown in FIG. 8, the error to flow learning unit 63 determines the percent pressure overshoot threshold level $HFFI_{OSPC\_LVL_K}$ and the percent pressure undershoot threshold level $HFFI_{USPC\_LVL_K}$. These values can be determined from calibration charts 93 and 95 that are a function of the operating frequency $FRQ_{SET}$, as expressed in the following functions:

$$HFFI_{OSPC\_LVL_K} = f(FRQ_{SET_K}) \quad (28).$$

$$HFFI_{USPC\_LVL_K} = f(FRQ_{SET_K}) \quad (29).$$

If a significant pressure overshoot exists $P_{EV\_HFFIPC\_OS_K} > HFFI_{OSPC\_LVL_K}$ (110), and has increased since the last cycle due to a reduction in flow ($P_{EV\_HFFIPC\_OS_K} = P_{EV\_HFFIPC\_OS_{K-1}}$) and $Q_{HFFI\_DLT_{K-1}} < 0$ (125) or decreased since the last cycle ($P_{EV\_HFFIPC\_OS_K} < P_{EV\_HFFIPC\_OS_{K-1}}$) (115), then the error to flow learning unit 63 adapts an increase in inspiratory flow (120) that is given by the following expression:

$$Q_{HFFI\text{-}DLT_K} = Q_{HFFI\_ADP\_OS_K} \qquad (30).$$

Otherwise, if a significant pressure undershoot exists $P_{EV\_HFFI\_US_K} > HFFI_{USPC\_LVL_K}$ (130), then the error to flow learning unit 63 adapts an increase in inspiratory flow (135) that is given by the following expression:

$$Q_{HFFI\_DLT_K} = Q_{HFFI\_ADP\_US_K} \qquad (31).$$

Otherwise, if the error at peak is outside the dead-band $|P_{EV\_HFFI\_ERR_K}| > HFFI_{ERR\_DBD}$ (140) then the error to flow learning unit 63 adapts an increase or decrease in inspiratory flow (145) that is given by the following relation:

$$Q_{HFFI\_DLT_K} = Q_{HFFI\_ADP\_ERR_K} \qquad (32).$$

In one embodiment, the AHFFI control system 13 also optimizes the inspiratory operating flow by determining the minimum flow required while minimizing the cycle errors. One reason to adapt a minimum inspiratory flow is to avoid wasting breathing gas which may be expensive (e.g. Heliox). If there is too much breathing gas in the patient respiratory ventilation system 11, the excess gas will be relieved by utilizing the exhalation valve. Hence, to optimize the use of breathing gas, the AHFFI control system 13 determines the minimum adaptive inspiratory flow required to minimize the cycle errors while achieving the desired pressure regulation requirements.

Next, the AHFFI control system 13 updates the adaptive inspiratory flow adjustment $Q_{HFFI\_ADP}$ using the delta AHFFI flow $Q_{HFFI\_DLT}$ (228). As shown in FIG. 5, the flow adjustment rate limiter 65 can be used to rate limit the allowed delta inspiratory flow servo target correction $Q_{HFFI\_DLT_K}$ per cycle. The flow adjustment rate limiter 65, receives the outputted results from the error to flow learning unit 63, and compares it to a maximum allowable delta inspiratory flow servo target correction $RT_{QSET\_HFFI}$, and outputs a computed delta inspiratory flow servo target correction $Q_{HFFI\_DLT}$, to the adder 67. In one embodiment, the maximum allowable delta inspiratory flow servo target correction $RT_{QSET\_HFFI}$ is set to one liter per minute correction per cycle. The delta inspiratory flow servo target correction $Q_{HIFF\_DLT_K}$ can be determined using the following expressions:

$$Q_{HFFI\_DLT_K} = \min(Q_{HFFI\_DLT_K}, RT_{QSET\_HFFI}) \qquad (33).$$

$$Q_{HFFI\_DLT_K} = \max(Q_{HFFI\_DLT_K}, -RT_{QSET\_HFFI}) \qquad (34).$$

The adder 67 receives the computed delta inspiratory flow servo target correction $Q_{HFFI\_DLT_K}$ and adds it to a one cycle delayed adaptive inspiratory flow adjustment $Q_{HFFI\_ADP_{K-1}}$, thus updating the adaptive inspiratory flow adjustment $Q_{HFFI\_ADP}$ for the current cycle as shown in the following expression:

$$Q_{HFFI\_ADP_K} = Q_{HFFI\_ADP_{K-1}} + Q_{HFFI\_DLT_K} \qquad (35).$$

The adder 67 outputs the result from Equation (35) to the limiter 69, which limits adaptive authority up to the maximum allowed inspiratory flow $Q_{INSP\_MAX}$ and no less than the negative of the feed-forward command so that the final flow is between zero and $Q_{INSP\_MAX}$, as determined from the following equations:

$$Q_{HFFI\_ADP_K} = \min(Q_{HFFI\_ADP_K}, (Q_{INSP\_MAX} - Q_{HFFI\_FFWD})) \qquad (36).$$

$$Q_{HFFI\_ADP_K} = \max(Q_{HFFI\_ADP_K}, -Q_{HFFI\_FFWD}) \qquad (37).$$

The AHFFI control system 13 then updates the final inspiratory operating flow servo target $Q_{HFFI\_CTL_K}$ by including the adaptive flow adjustment (230). The adder 47 combines the open-loop inspiratory flow adjustment $Q_{HFFI\_FFWD_K}$ with the closed-loop adaptive inspiratory flow $Q_{HFFI\_ADP_K}$, as expressed by the following equation:

$$Q_{HFFI\_CTL_K} = Q_{HFFI\_FFWD_K} + Q_{HFFI\_ADP_K} \qquad (38).$$

The adder 47 outputs the combined flow $Q_{HFFI\_CTL_K}$ to the limiter 51, which utilizes Equations (39) and (40) to limit the flow $Q_{HFFI\_CTL_K}$ between zero and the maximum allowable inspiratory flow command $Q_{INSP\_MAX}$, and outputs an inspiratory flow servo target $Q_{HFFI\_CTL_K}$ commanded by the AHFFI control system 13 to the comparator 49.

$$Q_{HFFI\_CTL_K} = \min(Q_{HFFI\_CTL_K}, Q_{INSP\_MAX}) \qquad (39).$$

$$Q_{HFFI\_CTL_K} = \max(Q_{HFFI\_CTL_K}, 0) \qquad (40).$$

The comparator 49 determines the greater flow demand between the inspiratory flow servo target $Q_{HFFI\_CTL}$ and the minimum user selected inspiratory flow $Q_{INSP\_MIN}$, and outputs the result $Q_{INSP\_DES}$ to the inspiratory flow servo controller 53.

Next, the AHFFI control system 13 resets the captured minimum/maximum AHFFI operating pressure targets, and the minimum/maximum measured WYE pressures from the last cycle as follows so that errors for the next cycle can be captured (232):

$$P_{EV\_DES\_MAX_{K-1}} = 0$$

$$P_{EV\_DES\_MIN_{K-1}} = P_{EV\_DES_K}$$

$$P_{WYE\_MAX_{K-1}} = 0$$

$$P_{WYE\_MIN_{K-1}} = P_{WYE\_PROC_K} \qquad (41).$$

The AHFFI control system 13 updates the maximum and minimum targets and pressures for the current cycle (250), and determines if the AHFFI control mode is disabled (252). If it is disabled, then the AHFFI control system 13 stops (254) its adaptive flow adjustment. However, if it is still active, then the AHFFI control system 13 resets the FCV and EV servo controllers (208) and repeats the entire process as shown in FIG. 9 until the AHFFI control mode is disabled (252).

In contrast, if the AHFFI control system 13 is operating at a start of a decreasing pressure target command (234), then the AHFFI control system 13 updates (236) the pressure error at peak command for a current cycle, according to the following equation:

$$P_{EV\_HFFI\_ERR_K} = P_{EV\_DES_K} - P_{WYE\_PROC_K} \qquad (42).$$

The error at peak is the pressure error from the operating pressure target when the peak command is given. However, if the AHFFI control system 13 is not operating at the start of a decreasing pressure command, then the AHFFI control system 13 holds the last pressure error for the current cycle $P_{EV\_HFFI\_ERR_K}$ (238) using the following expression:

$$P_{EV\_HFFI\_ERR_K} = P_{EV\_ERR_{K-1}} \qquad (43).$$

Next, regardless of whether the error at peak was updated or held, the AHFFI control system 13 holds the last feed-forward AHFFI flow command for the current cycle (240), such that:

$$Q_{HFFI\_FFWD_K} = Q_{HFFI\_FFWD_{K-1}} \quad (44)$$

The errors from the last cycle are held in the current cycle (242), unless they are due for updating (e.g. start of next cycle). Hence, the cycle errors are set to the following conditions:

$$P_{EV\_HFFI\_OS_K} = P_{EV\_HFFI\_OS_{K-1}} \quad (45)$$

$$P_{EV\_HFFI\_US_K} = P_{EV\_HFFI\_US_{K-1}} \quad (46)$$

$$P_{EV\_HFFIPC\_OS_K} = P_{EV\_HFFIPC\_OS_{K-1}} \quad (47)$$

$$P_{EV\_HFFIPC\_US_K} = P_{EV\_HFFIPC\_US_{K-1}} \quad (48)$$

Similarly, the AHFFI delta flow correction $Q_{HFFI\_DLT_K}$ (244), the adaptive inspiratory flow adjustment $Q_{HFFI\_ADP_K}$ (246), and the last computed AHFFI inspiratory operating flow target $Q_{HFFI\_CTL_K}$ (248) are held until it is time to update at the start of next cycle, such that:

$$Q_{HFFI\_DLT_K} = Q_{HFFI\_DLT_{K-1}} \quad (49)$$

$$Q_{HFFI\_ADP_K} = Q_{HFFI\_ADP_{K-1}} \quad (50)$$

$$Q_{HFFI\_CTL_K} = Q_{HFFI\_CTL_{K-1}} \quad (51)$$

Next, the AHFFI control system 13 updates the maximum and minimum targets and pressures for the current cycle (250), according to the following equations:

$$P_{EV\_DES\_MAX_K} = \max(P_{EV\_DES\_MAX_{K-1}}, P_{EV\_DES_K}) \quad (52)$$

$$P_{EV\_DES\_MIN_K} = \min(P_{EV\_DES\_MIN_{K-1}}, P_{EV\_DES_K}) \quad (53)$$

$$P_{WYE\_MAX_K} = \max(P_{WYE\_MAX_{K-1}}, P_{WYE\_PROC_K}) \quad (54)$$

$$P_{WYE\_MIN_K} = \min(P_{WYE\_MIN_{K-1}}, P_{WYE\_PROC_K}) \quad (55)$$

Finally, the AHFFI control system 13 determines if the AHFFI control mode is disabled (252). If it is disabled, then the AHFFI control system 13 stops (254) its adaptive flow adjustment. However, if it is still active, then the AHFFI control system 13 resets the FCV and EV servo controllers (208) and repeats the entire process as shown in FIG. 9 until the AHFFI control mode is disabled (252).

While certain exemplary embodiments have been described and shown in the accompanying drawings, it is to be understood that such embodiments are merely illustrative of and not restrictive on the broad invention. For example, a person skilled in the art can change the order of steps, for achieving an adaptive high frequency flow interrupter control system, without departing from the scope and spirit of the invention.

Furthermore, while the AHFFI control system 13 is described in the context of a patient respiratory ventilation system 11, the AHFFI control system 13 can be used for other applications that require an adaptive system approach for optimizing system conditions. Those skilled in the art will appreciate that various adaptations and modifications of the just described preferred embodiments can be configured without departing from the scope and spirit of the invention.

What is claimed is:

1. An adaptive high frequency flow interrupter control system comprising:
   a ventilator for supplying fluid;
   a flow servo controller for regulating fluid flow;
   a pressure servo controller for regulating fluid pressure;
   a means for receiving a precondition pressure wave function, representative of a precondition frequency, a precondition amplitude and a precondition pressure of the fluid flow in the adaptive high frequency flow interrupter control system;
   a means for establishing an operating pressure wave function, representative of an operating frequency, an operating amplitude and an operating pressure for operating flow desired in the adaptive high frequency flow interrupter control system;
   a means for determining cycle error between the precondition pressure wave function and the operating pressure wave function;
   a means for converting the cycle error to a flow adjustment; and
   a means for updating the operating flow with the flow adjustment.

2. The adaptive high frequency flow interrupter control system of claim 1, further comprising a means for delaying the updating means by a first cycle to provide a flow adjustment relative to a second cycle.

3. The adaptive high frequency flow interrupter control system of claim 1, further comprising a means for rate limiting the flow adjustment to provide a smooth transition between the fluid flow and the operating flow.

4. The adaptive high frequency flow interrupter control system of claim 1, further comprising:
   a means for establishing a feed-forward flow from the operating frequency and the operating amplitude; and
   a means for adding the feed-forward flow to the flow adjustment for updating the operating flow.

5. The adaptive high frequency flow interrupter control system of claim 1, further comprising:
   a means for establishing a minimum operating flow for the adaptive high frequency flow interrupter control system; and
   a means for limiting the updated operating flow to no less than the minimum operating flow.

6. The adaptive high frequency flow interrupter control system of claim 1, wherein the cycle error is selected from a group consisting of overshoot past the operating pressure wave function, undershoot past the operating pressure wave function and error at peak of the operating pressure wave function.

7. The adaptive high frequency flow interrupter control system of claim 1, further comprising a means for initializing operating pressure conditions of the adaptive high frequency flow interrupter control system as follows:

$$P_{EV\_DES\_MAX_{K-1}} = 0$$

$$P_{EV\_DES\_MIN_{K-1}} = P_{EV\_DES_K}$$

$$P_{WYE\_MAX_{K-1}} = 0$$

$$P_{WYE\_MIN_{K-1}} = P_{WYE\_PROC_K}$$

$$P_{EV\_HFFI\_OS_{K-1}} = 0$$

$$P_{EV\_HFFI\_US_{K-1}} = 0$$

$$P_{EV\_HFFI\_ERR_{K-1}} = 0$$

$$P_{EV\_HFFIPC\_OS_{K-1}} = 0$$

$$P_{EV\_HFFIPC\_US_{K-1}} = 0$$

where,
- $P_{EV\_DES\_MAX_{K-1}}$ is the K−1 sample of the maximum operating pressure;
- $P_{EV\_DES\_MIN_{K-1}}$ is the K−1 sample of the minimum operating pressure;
- $P_{EV\_DES_K}$ is the K sample of the operating pressure;
- $P_{WYE\_MAX_{K-1}}$ is the K−1 sample of the maximum precondition pressure;
- $P_{WYE\_MIN_{K-1}}$ is the K−1 sample of the minimum precondition pressure;
- $P_{WYE\_PROC_K}$ is the K sample of the precondition pressure;
- $P_{EV\_HFFI\_OS_{K-1}}$ is the K−1 sample of the pressure overshoot past the maximum operating pressure;
- $P_{EV\_HFFI\_US_{K-1}}$ is the K−1 sample of the pressure undershoot past the minimum operating pressure;
- $P_{EV\_HFFI\_ERR_{K-1}}$ is the K−1 sample of the pressure error when the maximum operating pressure is commanded;
- $P_{EV\_HFFIPC\_OS_{K-1}}$ is the K−1 sample of the percent pressure overshoot past the maximum operating pressure;
- $P_{EV\_HFFI\_US_{K-1}}$ is the K−1 sample of the percent pressure undershoot past the minimum operating pressure;
- K is the sample number at a given time during operation; and
- K−1 is the sample number before the K sample.

8. The adaptive high frequency flow interrupter control system of claim 1, further comprising a means for initializing operating flow conditions of the adaptive high frequency flow interrupter control system as follows:

$$Q_{HFFI\_ADP_{K-1}}=0$$

$$Q_{HFFI\_CTL_{K-1}}=0$$

$$Q_{HFFI\_FFWD_{K-1}}=0$$

where,
- $Q_{HFFI\_ADP_{K-1}}$ is the K−1 sample of the flow adjustment;
- $Q_{HFFI\_CTL_{K-1}}$ is the K−1 sample of the operating flow;
- $Q_{HFFI\_FFWD_{K-1}}$ is the K−1 sample of the feed-forward flow;
- K is the sample number at a given time during operation; and
- K−1 is the sample number before the K sample.

9. The adaptive high frequency flow interrupter control system of claim 1, wherein the operating pressure wave function is determined from the following expression, $$P_{EV\_DES_K}=A_{SET\,K}*\sin(2\cdot\pi\cdot FRQ_{SET\,K})+\max(P_{EV\_MAP_K},A_{SET\,K})$$

where,
- $P_{EV\_DES_K}$ is the K sample operating pressure;
- $A_{SET\,K}$ is the K sample operating pressure;
- $FRQ_{SET\,K}$ is the K sample operating frequency;
- $P_{EV\_MAP_K}$ is the K sample mean operating pressure; and
- K is the sample number at a given time during operation.

10. The adaptive high frequency flow interrupter control system of claim 6, wherein the cycle error for the overshoot past the operating pressure wave function is determined from the following expression, $$P_{EV\_HFFI\_OS_K}=\max(0,(P_{WYE\_MAX_{K-1}}-P_{EV\_DES\_MAX_{K-1}}))$$

and for the undershoot past the operating pressure wave function is determined from the following expression, $$P_{EV\_HFFI\_US_E}=\max(0,(P_{EV\_DES\_MIN_{K-1}}-P_{WYE\_MIN_{K-1}}))$$

where,
- $P_{EV\_DES\_MAX_{K-1}}$ is the maximum operating pressure during a K−1 sample;
- $P_{EV\_DES\_MIN_{K-1}}$ is the minimum operating pressure during a K−1 sample;
- $P_{WYE\_MAX_{K-1}}$ is the maximum precondition pressure during a K−1 sample;
- $P_{WYE\_MIN_{K-1}}$ is the minimum precondition pressure during a K−1 sample,
- $P_{EV\_HFFI\_OS_{K-1}}$ is the pressure overshoot past the maximum operating pressure during a K−1 sample;
- $P_{EV\_HFFI\_US_{K-1}}$ is the pressure undershoot past the minimum operating pressure during a K−1 sample;
- K is the sample number at a given time during operation; and
- K−1 is the sample number before the K sample.

11. The adaptive high frequency flow interrupter control system of claim 10, wherein the flow adjustment for the overshoot past the operating pressure wave function is determined from the following expression, $$Q_{HFFI\_ADP\_OS_K}=HFFI_{OS2\_QINSP}*P_{EV\_HFFI\_OS_K}$$

and for the undershoot past the operating pressure wave function is determined from the following expression, $$Q_{HFFI\_ADP\_US_K}=HFFI_{US2\_QINSP}*P_{EV\_HFFI\_US_K}$$

where,
- $Q_{HFFI\_ADP\_OS_K}$ is the flow adjustment for the pressure overshoot during a K sample;
- $HFFI_{OS2\_QINSP}$ is the gain used to convert pressure overshoot to the flow adjustment for the pressure overshoot;
- $P_{EV\_HFFI\_OS_K}$ is the pressure overshoot past the maximum operating pressure during a K sample;
- $Q_{HFFI\_ADP\_US_K}$ is the flow adjustment for the pressure undershoot during a K sample;
- $HFFI_{US2\_QINSP}$ is the gain used to convert pressure undershoot to the flow adjustment for the pressure undershoot; and
- $P_{EV\_HFFI\_US_K}$ is the pressure undershoot past the minimum operating pressure during a K sample.

12. The adaptive high frequency flow interrupter control system of claim 6, wherein the cycle error for the error at peak of the operating pressure wave function is determined from the following expression, $$P_{EV\_HFFI\_ERR_K}=P_{EV\_DES_K}-P_{WYE\_PROC_K}$$

where
- $P_{EV\_DES_K}$ is the operating pressure during a K sample;
- $P_{WYE\_PROC_K}$ is the precondition pressure during a K sample;
- $P_{EV\_HFFI\_ERR_K}$ is the pressure error when the maximum operating pressure is commanded during a K sample; and
- K is the sample number at a given time during operation.

13. The adaptive high frequency flow interrupter control system of claim 6, wherein the flow adjustment for the error at peak of the operating pressure wave function is maintained from a previous cycle.

14. An adaptive high frequency flow interrupter control system comprising:
- a ventilator for supplying fluid;
- a flow servo controller for regulating fluid flow;
- a pressure servo controller for regulating fluid pressure;
- a cycle error measurement unit for receiving a precondition pressure wave function, representative of a precondition frequency, a precondition amplitude and a precondition pressure of the fluid flow, establishing an operating pressure wave function, representative of an operating frequency, an operating amplitude and an operating pressure of for operating flow desired, and for determining cycle error between the precondition pressure wave function and the operating pressure wave function; and an error to flow learning unit for converting the cycle error to a flow adjustment for use in adjusting the operating flow.

15. The adaptive high frequency flow interrupter control system of claim 14, wherein the operating flow is optimized to provide minimal operating flow that satisfies the operating pressure wave function.

16. The adaptive high frequency flow interrupter control system of claim 14, further comprising a sample delay unit for delaying the flow adjustment by a cycle.

17. The adaptive high frequency flow interrupter control system of claim 14, further comprising a flow adjustment rate limiter adapted to provide a smooth transition between the fluid flow and the operating flow.

18. The adaptive high frequency flow interrupter control system of claim 14, further comprising:
 a means for establishing a feed-forward flow from the operating frequency and the operating amplitude; and
 an adder for adding the feed-forward flow to the flow adjustment for adjusting the operating flow.

19. The adaptive high frequency flow interrupter control system of claim 14, further comprising a limiter for limiting the adjusted operating flow to no less than a predetermined minimum operating flow.

20. The adaptive high frequency flow interrupter control system of claim 14, wherein the cycle error is selected from a group consisting of overshoot past the operating pressure wave function, undershoot past the operating pressure wave function and error at peak of the operating pressure wave function.

21. The adaptive high frequency flow interrupter control system of claim 14, further comprising a means for initializing operating pressure conditions of the adaptive high frequency flow interrupter control system as follows:

$$P_{EV\_DES\_MAX_{K-1}}=0$$

$$P_{EV\_DES\_MIN_{K-1}}=P_{EV\_DES_K}$$

$$P_{WYE\_MAX_{K-1}}=0$$

$$P_{WYE\_MIN_{K-1}}=P_{WYE\_PROC_K}$$

$$P_{EV\_HFFI\_OS_{K-1}}=0$$

$$P_{EV\_HFFI\_US_{K-1}}=0$$

$$P_{EV\_HFFI\_ERR_{K-1}}=0$$

$$P_{EV\_HFFIPC\_OS_{K-1}}=0$$

$$P_{EV\_HFFIPC\_US_{K-1}}=0$$

where,
 $P_{EV\_DES\_MAX_{K-1}}$ is the maximum operating pressure during a K-1 sample;
 $P_{EV\_DES\_MIN_{K-1}}$ is the minimum operating pressure during a K-1 sample;
 $P_{EV\_DES_K}$ is the operating pressure during a K sample;
 $P_{WYE\_MAX_{K-1}}$ is the maximum precondition pressure during a K-1 sample;
 $P_{WYE\_MIN_{K-1}}$ is the minimum precondition pressure during a K-1 sample;
 $P_{WYE\_PROC_K}$ is the precondition pressure during a K sample;
 $P_{EV\_HFFI\_OS_{K-1}}$ is the pressure overshoot past the maximum operating pressure during a K-1 sample;
 $P_{EV\_HFFI\_US_{K-1}}$ is the pressure undershoot past the minimum operating pressure during a K-1 sample;
 $P_{EV\_HFFI\_ERR_{K-1}}$ is the pressure error when the maximum operating pressure is commanded during a K-1 sample;
 $P_{EV\_HFFIPC\_OS_{K-1}}$ is the percent pressure overshoot past the maximum operating pressure during a K-1 sample;
 $P_{EV\_HFFI\_US_{K-1}}$ is the percent pressure overshoot past the minimum operating pressure during a K-1 sample;
 K is the sample number at a given time during operation; and
 K-1 is the sample number before the K sample.

22. The adaptive high frequency flow interrupter control system of claim 14, further comprising a means for initializing operating flow conditions of the adaptive high frequency flow interrupter control system as follows:

$$Q_{HFFI\_ADP_{K-1}}=0$$

$$Q_{HFFI\_CTL_{K-1}}=0$$

$$Q_{HFFI\_FFWD_{K-1}}=0$$

where,
 $Q_{HFFI\_ADP_{K-1}}$ is the flow adjustment during a K-1 sample;
 $Q_{HFFI\_CTL_{K-1}}$ is the operating flow during a K-1 sample;
 $Q_{HFFI\_FFWD_{K-1}}$ is the feed-forward flow during a K-1 sample;
 K is the sample number at a given time during operation; and
 K-1 is the sample number before the K sample.

23. The adaptive high frequency flow interrupter control system of claim 14, wherein the operating pressure wave function is determined from the following expression, $$P_{EV\_DES_K}=A_{SET\,K}*\sin(2\cdot\pi\cdot FRQ_{SET\,K})+\max(P_{EV\_MAP_K},A_{SET\,K})$$

where,
 $P_{EV\_DES_K}$ is the operating pressure during a K sample;
 $A_{SET\,K}$ is the operating pressure during a K sample;
 $FRQ_{SET\,K}$ is the operating frequency during a K sample;
 $P_{EV\_MAP_K}$ is the mean operating pressure during a K sample; and
 K is the sample number at a given time during operation.

24. The adaptive high frequency flow interrupter control system of claim 20, wherein the cycle error for the overshoot past the operating pressure wave function is determined from the following expression, $$P_{EV\_HFFI\_OS_K}=\max(0,(P_{WYE\_MAX_{K-1}}-P_{EV\_DES\_MAX_{K-1}}))$$

and for the undershoot past the operating pressure wave function is determined from the following expression, $$P_{EV\_HFFI\_US_E}=\max(0,(P_{EV\_DES\_MIN_{K-1}}-P_{WYE\_MIN_{K-1}}))$$

where,
 $P_{EV\_DES\_MAX_{K-1}}$ is the maximum operating pressure during a K-1 sample;
 $P_{EV\_DES\_MIN_{K-1}}$ is the minimum operating pressure during a K-1 sample;
 $P_{WYE\_MAX_{K-1}}$ is the maximum precondition pressure during a K-1 sample;

$P_{WYE\_MIN_{K-1}}$ is the minimum precondition pressure during a K−1 sample, $P_{EV\_HFFI\_OS_{K-1}}$ is the pressure overshoot past the maximum operating pressure during a K sample;

$P_{EV\_HFFI\_US}$ is the pressure undershoot past the minimum operating pressure during a K sample;

K is the sample number at a given time during operation; and

K−1 is the sample number before the K sample.

25. The adaptive high frequency flow interrupter control system of claim 24, wherein a percent cycle error for the overshoot past the operating pressure wave function is determined from the following expression, $$P_{EV\_HFFIPC\_OS_K} = \max\left(0, \left(\frac{2*P_{EV\_HFFI\_OS_K}}{P_{EV\_DES\_MAX_{K-1}} - P_{EV\_DES\_MIN_{K-1}}}\right)\right)$$

and for the undershoot past the operating pressure wave function is determined from the following expression, $$P_{EV\_HFFIPC\_US_K} = \max\left(0, \left(\frac{2*P_{EV\_HFFI\_US_K}}{P_{EV\_DES\_MAX_{K-1}} - P_{EV\_DES\_MIN_{K-1}}}\right)\right)$$

where, $P_{EV\_DES\_MAX_{K-1}}$ is the maximum operating pressure during a K−1 sample;

$P_{EV\_DES\_MIN_{K-1}}$ is the minimum operating pressure during a K−1 sample;

$P_{EV\_HFFI\_OS_K}$ is the pressure overshoot past the maximum operating pressure during a K sample;

$P_{EV\_HFFI\_US_{K-1}}$ is the pressure undershoot past the minimum operating pressure during a K sample;

$P_{EV\_HFFIPC\_OS_K}$ is the percent pressure overshoot past the maximum operating pressure during a K sample;

$P_{EV\_HFFIPC\_US_K}$ is the percent pressure undershoot past the minimum operating pressure during a K sample;

K is the sample number at a given time during operation; and

K−1 is the sample number before the K sample.

26. The adaptive high frequency flow interrupter control system of claim 25, wherein the flow adjustment for the overshoot past the operating pressure wave function is determined from the following expression, $$Q_{HFFI\_ADP\_OS_K} = HFFI_{OS2\_QINSP} * P_{EV\_HFFI\_OS_K}$$

and for the undershoot past the operating pressure wave function is determined from the following expression, $$Q_{HFFI\_ADP\_US_K} = HFFI_{US2\_QINSP} * P_{EV\_HFFI\_US_K}$$

where, $Q_{HFFI\_ADP\_OS_K}$ is the flow adjustment for the pressure overshoot during a K sample;

$HFFI_{OS2\_QINSP}$ is the gain used to convert pressure overshoot to the flow adjustment for the pressure overshoot;

$P_{EV\_HFFI\_OS_K}$ is the pressure overshoot past the maximum operating pressure during a K sample;

$Q_{HFFI\_ADP\_US_K}$ is the flow adjustment for the pressure undershoot during a K sample;

$HFFI_{US2\_QINSP}$ is the gain used to convert pressure undershoot to the flow adjustment for the pressure undershoot; and $P_{EV\_HFFI\_US_K}$ is the pressure undershoot past the minimum operating pressure during a K sample.

27. The adaptive high frequency flow interrupter control system of claim 20, wherein the cycle error for the error at peak of the operating pressure wave function is determined from the following expression, $$P_{EV\_HFFI\_ERR_K} = P_{EV\_DES_K} - P_{WYE\_PROC_K}$$

where $P_{EV\_DES_K}$ is the operating pressure during a K sample;

$P_{WYE\_PROC_K}$ is the precondition pressure during a K sample;

$P_{EV\_HFFI\_ERR_K}$ is the pressure error when the maximum operating pressure is commanded during a K sample; and K is the sample number at a given time during operation; and K−1 is the sample number before the K sample.

28. The adaptive high frequency flow interrupter control system of claim 20, wherein the flow adjustment for the error at peak of the operating pressure wave function is maintained from a previous cycle.

* * * * *